United States Patent [19]
Taylor et al.

[11] Patent Number: 5,941,912
[45] Date of Patent: Aug. 24, 1999

[54] PROSTHETIC JOINT CONNECTOR ASSEMBLY

[75] Inventors: Douglas A. Taylor, 7823 Lovage Ct., Indianapolis, Ind. 46237; Chris L. Johnson, Plainwell, Mich.

[73] Assignee: Douglas A. Taylor, Indianapolis, Ind.

[21] Appl. No.: 09/077,491
[22] PCT Filed: Nov. 29, 1995
[86] PCT No.: PCT/US95/15451
  § 371 Date: May 29, 1998
  § 102(e) Date: May 29, 1998
[87] PCT Pub. No.: WO96/16614
  PCT Pub. Date: Jun. 6, 1996

[51] Int. Cl.⁶ .................................................. A61F 2/60
[52] U.S. Cl. ........................................................ 623/28
[58] Field of Search ................................ 623/38; 403/87, 403/90, 82

[56] References Cited

U.S. PATENT DOCUMENTS

| | | | |
|---|---|---|---|
| 3,538,516 | 11/1970 | Bailey et al. | 623/38 |
| 4,475,546 | 10/1984 | Patton | 606/57 |
| 5,545,231 | 8/1996 | Houser | 623/38 |
| 5,888,232 | 3/1999 | Taylor | 623/38 |

FOREIGN PATENT DOCUMENTS 2169207  7/1986  United Kingdom .................. 623/38

*Primary Examiner*—Todd E. Manahan
*Assistant Examiner*—Eduardo C. Robert
*Attorney, Agent, or Firm*—Bingham Summers Welsh & Spilman; Daniel L. Boots

[57] ABSTRACT

A prosthetic joint connector assembly includes a pylon having a first end and an outwardly flared portion adjacent to a second end thereof. The second end of the pylon is closed by a convexly domed surface which forms a concave interior surface and has a generally axial opening formed therein. The prosthetic joint connector further includes a securing nut carried internally of the pylon and an abutment also carried internally of the pylon. The securing nut is defined by a cylindrical member having a first end and an outwardly flared portion adjacent to a second end which terminates in a convexly domed surface. The securing nut also has an internally threaded axial bore extending at least partially therethrough. The first end of the securing nut has a bearing surface for engaging the abutment such that the securing nut is interposed between the abutment and the concave interior surface of the second end of the pylon. The securing nut, when unsecured, is free to pivot about the abutment at its first end and to, at its second end, slidingly move relative to the concave interior surface of the second end of the pylon.

20 Claims, 9 Drawing Sheets

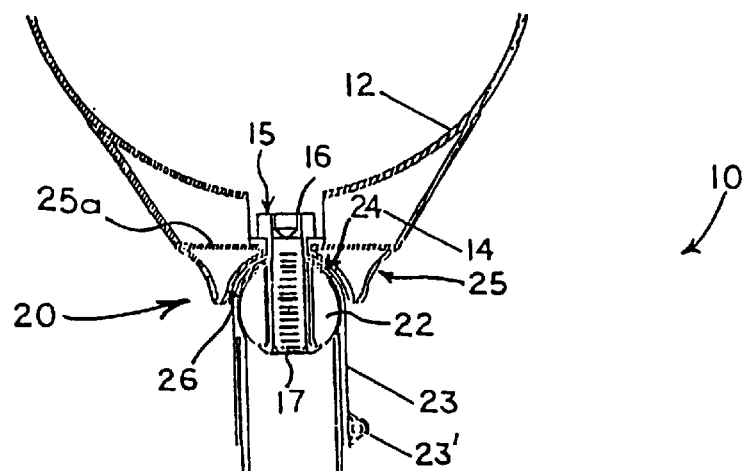
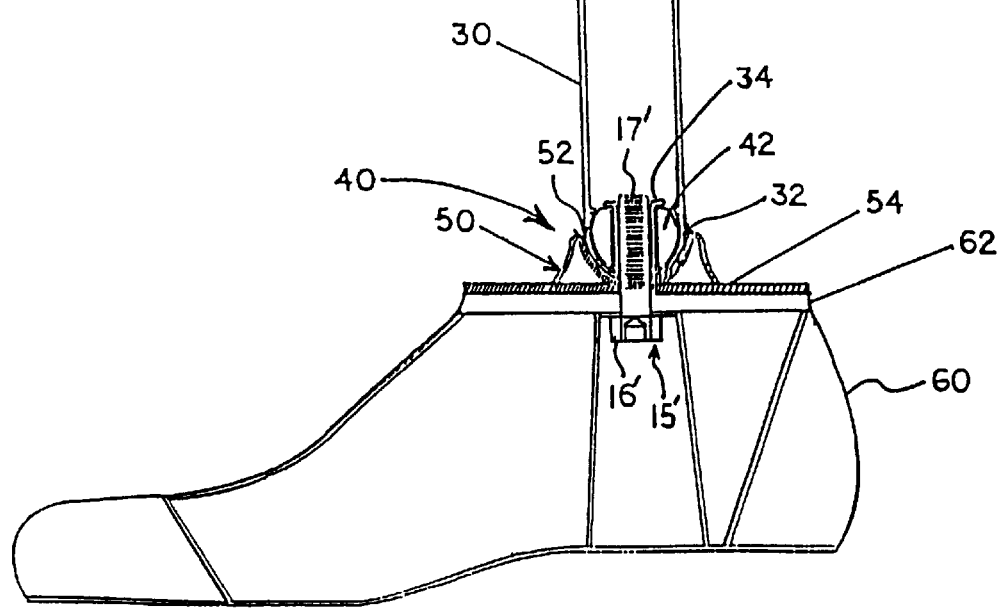
FIG. 1

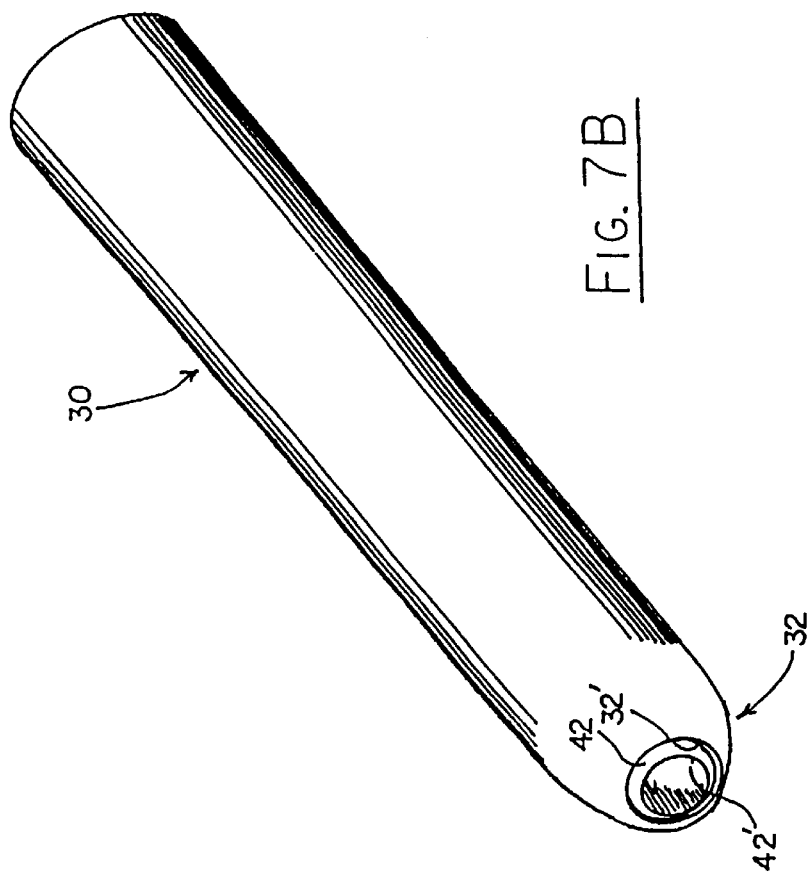
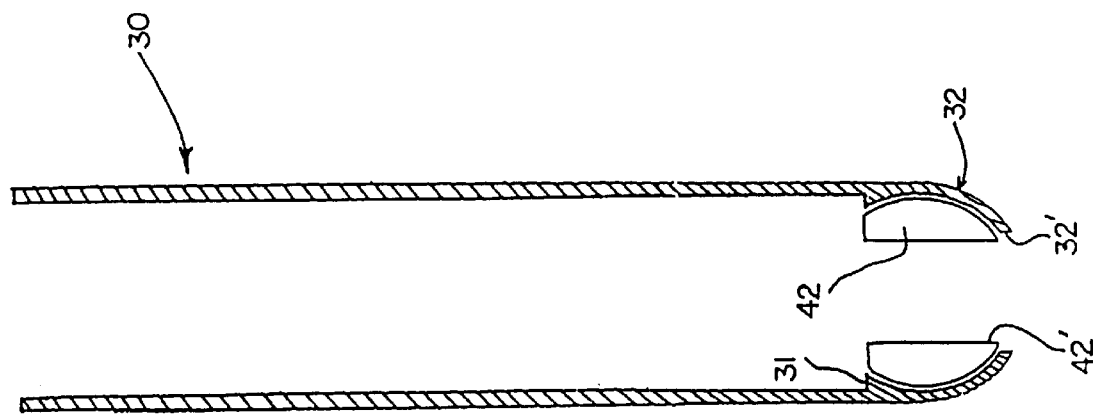
FIG. 7B
FIG. 7A

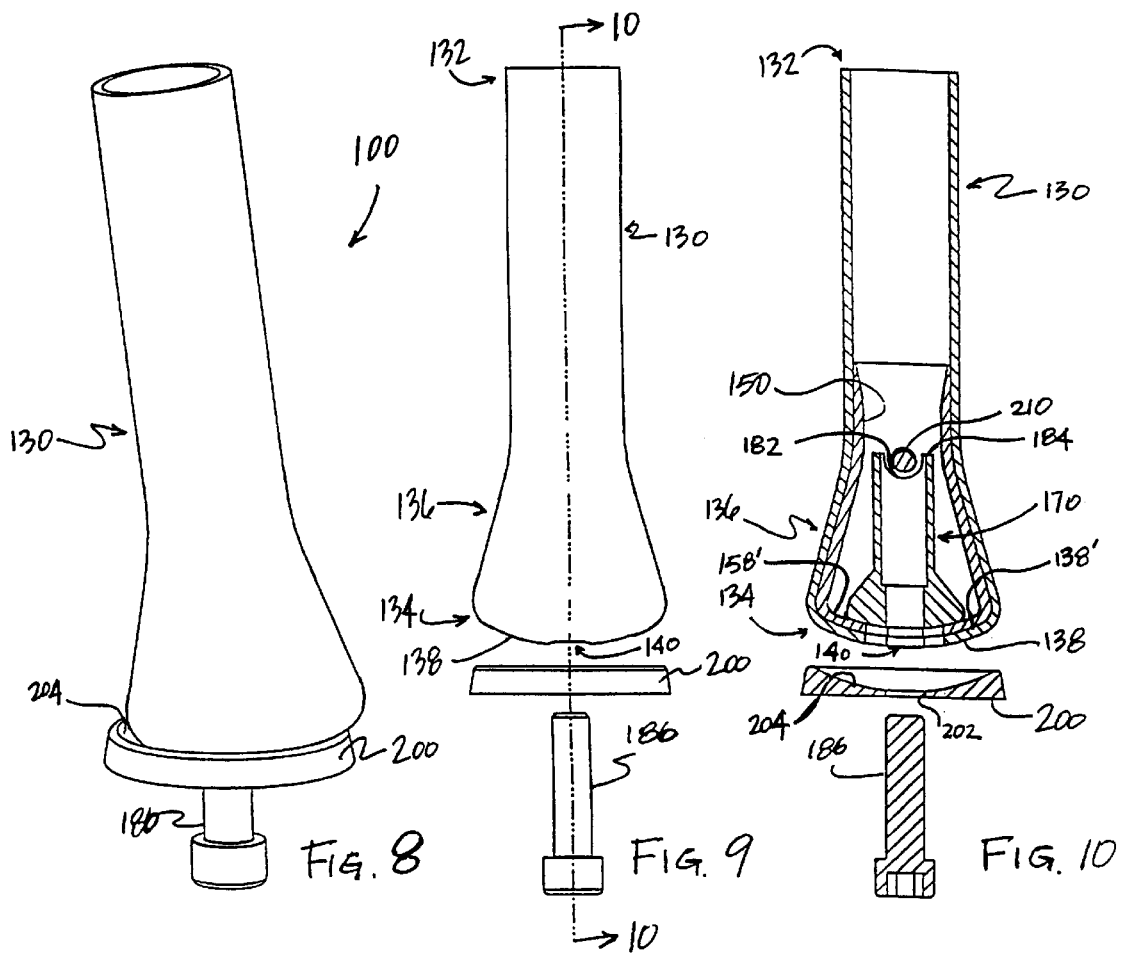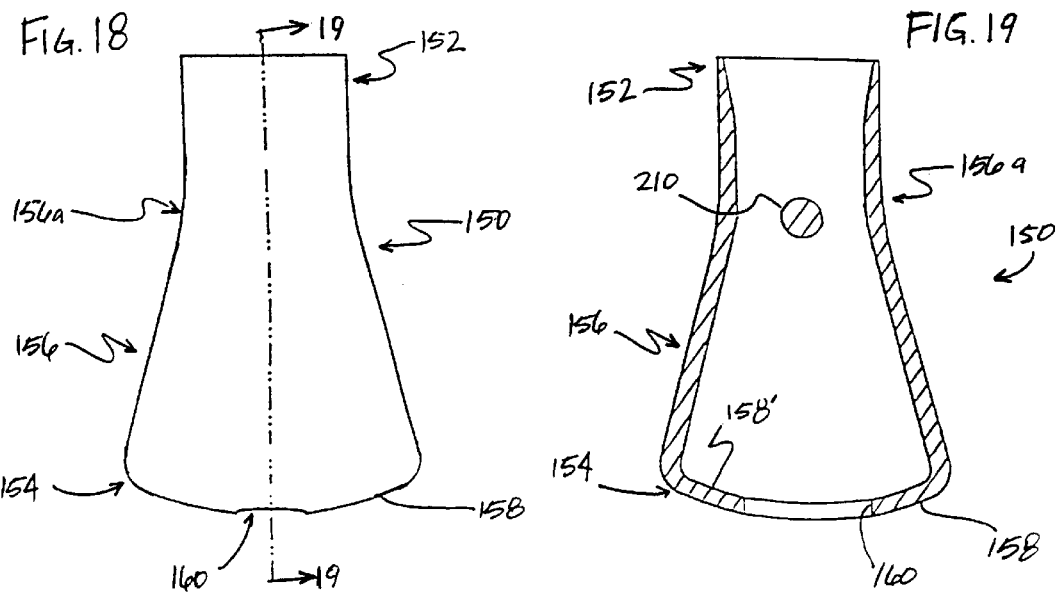

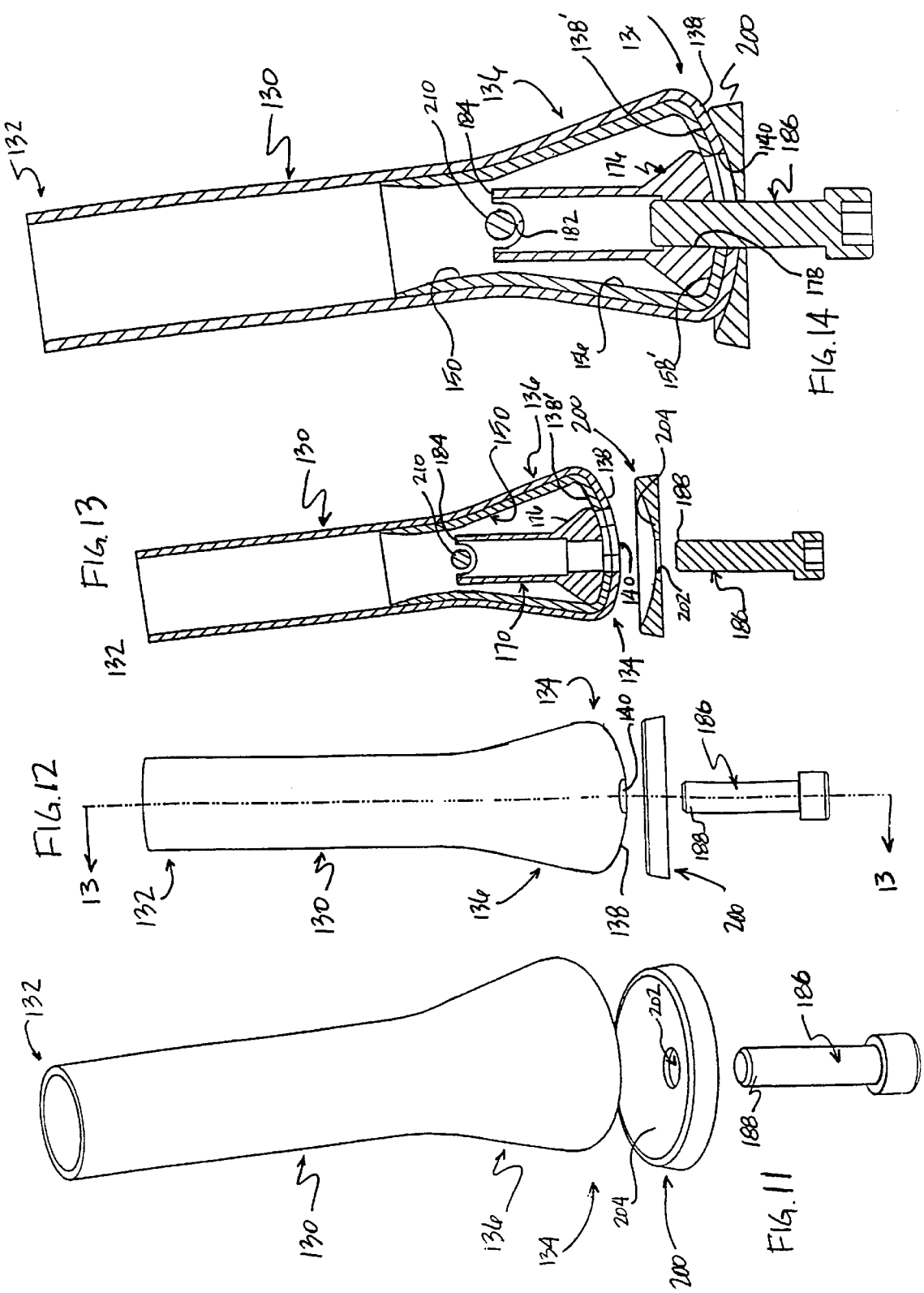

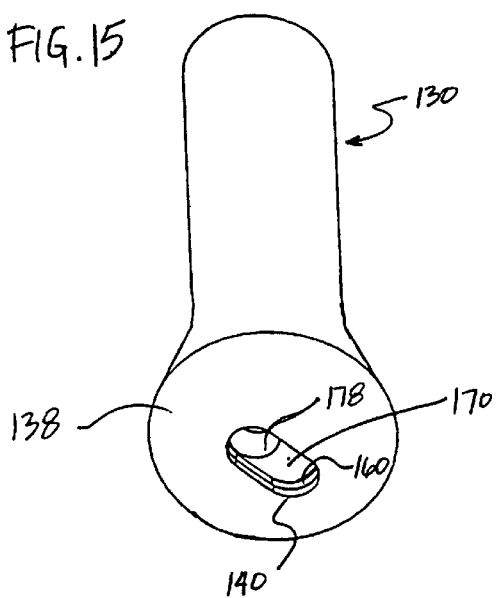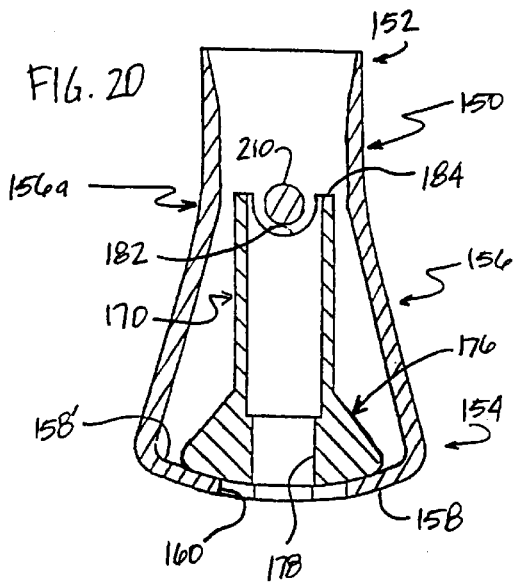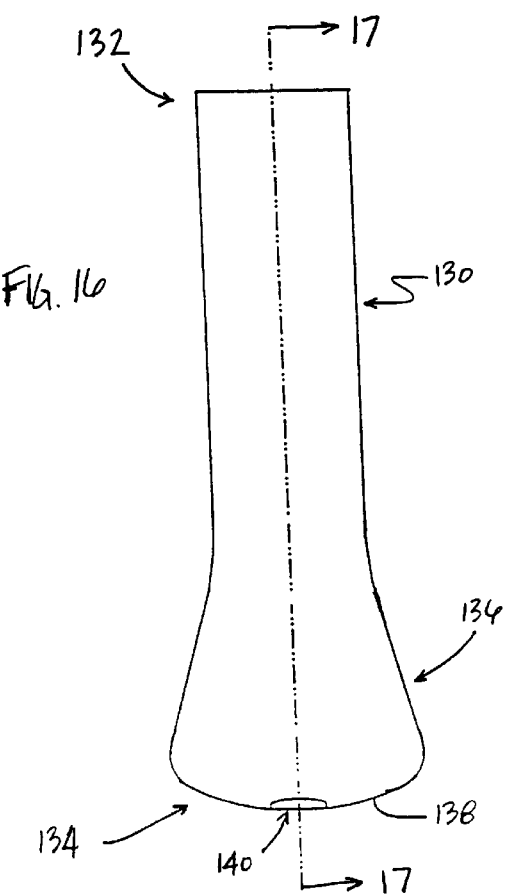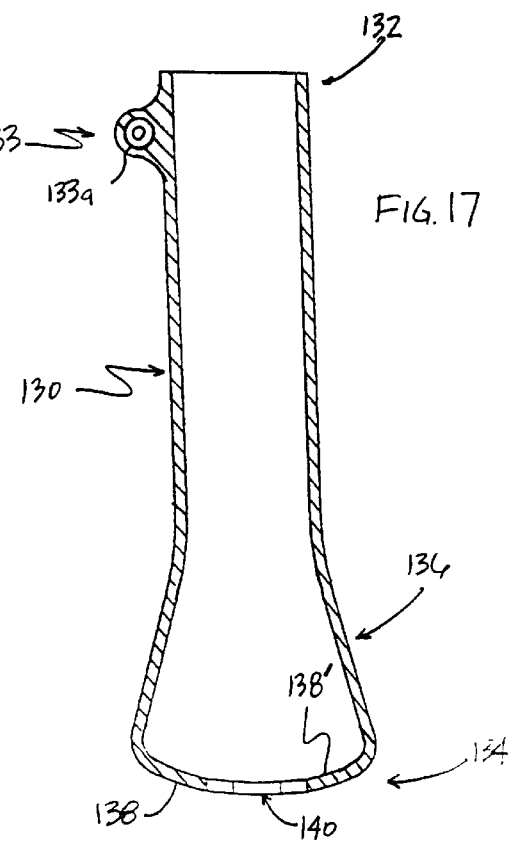

PROSTHETIC JOINT CONNECTOR ASSEMBLY

TECHNICAL FIELD

This invention relates to connectors and, more particularly, to quick-adjusting connector assemblies especially useful in prosthetic limb systems.

BACKGROUND ART

Prosthetic limbs must be custom made because of the individual deviation in height and weight of each person and the individual idiosyncratic physiological condition of the person's residual limb including, but not limited to, the length of the residual limb, the possible weight fluctuations thereof and the atrophy of the limb that typically occurs after amputation. Moreover, the residual limb commonly changes shape due to the changes in swelling during the healing process. Because each prosthetic limb must be custom made to accommodate these individual conditions, such limbs cannot be mass produced, which considerably increases their costs.

In fitting a patient with a prosthesis following an amputation of a lower limb, the prosthetist must ensure the prosthesis swings substantially in the sagittal plane during walking by the patient. The body of the patient and his attitude or gait when walking typically require certain adjustments in the relative positioning of various components of the prosthetic device. These adjustments are frequently made in two orthogonal places—the anterior-posterior plane and in the lateral-medial plane. During the initial fitting, the prosthetist typically builds up an artificial limb utilizing adjustable elements in accord with the length and orientation of the patient's body. The final prosthetic device, however, is commonly permanently fixed at the various joints, thus precluding any further or later adjustment. An improper adjustment means that the patient wearing the leg prosthesis binds the leg unnaturally, which results in an unnatural movement pattern during walking. Nevertheless, even with the best initial fitting, the patient, while adapting to the artificial limb, may change his stance or gait to the extent that, for example, flexion of the knee joint no longer occurs in the sagittal plane. This is difficult to accommodate in a permanently bonded artificial limb, particularly when the prosthetic socket, normally molded to fit the patient's residual limb, is fixed to the remaining portion of the prosthesis.

Some adjustable fittings or connectors are available in the prior art to permit separation of the molded socket from the prosthesis to permit incremental rotation of the inferior portion of the prosthesis relative to the socket. Certain prior art devices also include later adjustment facilities to allow for the adjustment of the angular attitude and position relative to the load line of the pylon tube after the prosthesis has been in use for some time. (The load line is an imaginary line extending between the foot joint and the knee along which, ideally, the body weight acts.)

Various prosthetic joints or connectors for an endoskeletal artificial leg are also well known. Such joints typically comprise an adjustable link designed to interconnect adjoining members of a prosthetic limb, such as a residual limb support, i.e., a prosthetic socket and a thigh member, a knee joint and a lower leg member, or at the ankle for connecting the lower end of a prosthesis to an artificial foot. The upper and/or lower portions of such an artificial joint is commonly provided with some means for adjustment.

One prior art system is the ball-and-socket type that permits appropriate flexion of the shin relative to the foot. Exemplary of such technology is Shorter et al., U.S. Pat. No. 4,463,459. Such ball-coupling arrangements, however, are generally of a heavy construction in order to achieve the required strength and stability while in use. The resulting heavy weight, however, is undesirable to the wearer as it causes undue energy expenditure and lack of control of the prosthetic device.

Moreover, various types of angle adjustment units are also known for adjusting the longitudinal axis of a prosthesis. Present modular prosthetic limb components commonly utilize frusto-pyramidal bosses and screws to affect angular adjustments in alignment and speed assembly procedures. Typically, a series of metal adapters and aluminum tubes are connected together to assembly the prosthetic structure. Such adapters employ only a relatively small surface area to interface parts. Consequently, heavy metals such as steel or titanium are typically used in such amounts that increase the weight of the device significantly. Thus, though such devices are manufactured for convenient later adjustability, they are not designed for minimum weight. Furthermore, these angular adjustment units are capable of transmitting only a relatively small momentum and are expensive to design and manufacture.

In any prosthetic device, it is desirable to decrease the weight of the elements in order to decrease the strain placed on the patient. Elimination of any unnecessary parts and the use of lighter materials to replace heavier components such as the connector joint or the pylon tube are particularly desirable objectives.

Some modular componentry, on the other hand, is relatively light in weight but lacks the desired adjustability. In the case of a modular below-knee (BK) prosthesis, the lightest a prosthetic device can be is about 3 pounds. For an above-knee (AK) prosthesis, the minimal weight is about 6 pounds to maintain full adjustability. This factor is significant because a prosthesis is considered "dead weight" (without sensation) to the patient. During the swing phase of gait, the prosthesis will tend to drop away from the patient's residual limb due to its weight. During the heel strike and stances phases, the prosthesis will tend to move upward until pressure equilibrium is attained. This results in considerable "pistoning" (up and down piston-like movements) of the prosthesis due to gravity, especially in the case of poor suspension of the prosthetic device from the residual limb. This pistoning action leads to lack of control and reduced proprioception. Reduction in weight can reduce or eliminate these problems by reducing the moment of inertia required to accelerate and decelerate the prosthesis.

Accordingly, there remains a need for a prosthetic device that is light in weight while sufficiently strong, that is economical to manufacture, and that readily allows for later adjustment of the device without damaging the physical integrity of the prosthetic device.

SUMMARY OF THE INVENTION

This invention presents a ultralight modular connector system especially useful in a modular prosthetic system that decreases the energy expended by the wearer and provides better comfort, control and mobility, thereby enhancing the quality of life of the amputee patient. The invention consolidates parts, reduces the amounts of heavy metals to a minimum, and significantly simplifies the alignment process. Moreover, the reduced weight of the resultant prosthetic device reduces the problems caused by the pistoning action of the device by reducing the moment of inertia required to accelerate/decelerate the device, which also leads to less random movement between the residual limb and the socket, thereby increasing the comfort to the wearer.

This invention provides a quick-adjusting modular prosthetic system including a first connector connected to one end of a tube member and a second connector connected to the opposite end of the tube member. When employed in such a prosthetic system, the first connector interconnects the tube member, such as a prosthetic pylon, to a socket for receiving a residual limb and the second connector interconnects the pylon to a prosthetic foot.

More particularly, the modular prosthetic system comprises a first prosthetic member such as a pylon tube having a first male end, an extending member such as a prosthetic bolt having a proximal end and a distal end, the first end of the first prosthetic member having an opening therein for receiving the distal end of the bolt, and a second prosthetic member for anchoring the proximal end of the prosthetic bolt. The prosthetic bolt is generally fixed in position relative to the second prosthetic member while the first prosthetic member is movable relative to the second prosthetic member. The prosthetic bolt may be tightened to releasably lock the first prosthetic member in a fixed position relative to the second prosthetic member. The first male end of the first member is preferably convexly hemispherical, and the second prosthetic member includes a concavely hemispherical seat for receiving the male end of the first prosthetic member. Thus, the novel connector system of this invention comprises a ball, a radiused-end socket and a seat that employs the single prosthetic bolt to lock and unlock the connector.

A further embodiment of the present invention provides a prosthetic joint connector system comprising a pylon, an insert carried internally of the pylon, a securing nut carried internally of the pylon, a securing bolt, and an external base member.

The pylon of this further embodiment has a generally cylindrical first end and an outwardly flared portion adjacent to its second end, which is partially closed by a convexly domed surface having a non-circular opening formed generally centrally therein. The convexly domed surface of the second end of the pylon concomitantly defines a concavely spherical interior surface.

The insert carried internally by the pylon also has a generally cylindrical first end and an outwardly flared portion adjacent to its second end. The second end of the insert is also partially closed by a convexly domed surface having an opening formed generally centrally therein. The opening in the second end of the insert generally corresponds in shape to the opening formed in the second end of the pylon. The convexly domed surface of the second end of the insert also defines a concavely spherical interior surface. The shape of the exterior of the insert corresponds to and fits snugly within the interior configuration of the flared second end of the pylon, and is permanently retained therein as a result of the filament winding process from which the pylon is preferably constructed. Accordingly, the convexly domed surface of the second end of the insert abuttingly engages the concave interior surface of the second end of the pylon. The first end of the insert extends partially through the tubular portion of the pylon toward the first end thereof.

The securing nut is preferably carried internally of the insert, and has a generally cylindrical body at a first end thereof, an outwardly flared portion at a second end thereof, and an internally threaded axial bore extending from the second end thereof and at least partially along a longitudinal axis of the nut toward its first end. The internally threaded axial bore is intended for receiving therein the externally threaded shank of the securing bolt. The second end of the nut also terminates in a convexly domed surface. When the nut is disposed internally of the insert, the convexly domed surface of the second end of the securing nut abuttingly engages the concave interior surface of the second end of the insert.

In this further embodiment, an abutment is disposed internally of the pylon at a point generally coinciding with the juncture between the tubular and outwardly flared portions of the pylon. The abutment is preferably defined by a transverse bar fixed in position extending diametrically across the interior of the insert. The securing nut is further provided with a bearing surface at its first end for pivotally engaging the abutment such that the securing nut is interposed between the abutment and the concave interior surface of the second end of the pylon. When not engaged by the securing bolt, the securing nut is free to pivot at its first end about the abutment in a swinging pendulum fashion and, at its second end, to slidingly engage and move relative to the concave interior surface of the second end of the pylon.

The external base member has a central opening therein through which the shank of the securing bolt extends, and a concavely spherical bearing surface for receiving the convexly domed exterior surface of the second end of the pylon. The base member is typically affixed to, or made an integral part of, an opposing prosthetic article, such as a prosthetic foot or limb socket.

In operation, once the prosthetist has determined the proper alignment of the artificial limb, the securing bolt can be rotated to be threadably received in the internally threaded axial bore of the securing nut to clamp with increasing force the second ends of the pylon and the insert between the domed second end of the securing nut and the concavely spherical bearing surface of the external base member. Tightening of the securing bolt releasably secures the pylon in position relative to the external base member to maintain the proper alignment of the prosthetic device.

All angular and rotational adjustments of the embodiments of this invention can be readily made by simply accessing the securing prosthetic bolt from outside the foam cover of the prosthesis.

The connector systems of this invention can also be employed in a light-weight structural network that can be collapsed and readily transported, such as those employed in the construction of space station structures. An ultralight collapsible wheelchair is another possible application of the connector systems of this invention.

Other novel features and advantages of the invention will be apparent from the drawings and detailed description that follows.

BRIEF DESCRIPTION OF THE DRAWINGS

FIG. 1 is a cross section of a prosthetic BK leg system constructed in accordance with the invention;

FIGS. 7A and 7B are cross-section and perspective views of a novel tubular member employed with the prosthetic connector system of this invention;

FIG. 8 is a perspective view of a further embodiment of a prosthetic joint connector assembly provided by this invention;

FIG. 9 is a plan view of the connector assembly of FIG. 8 shown in an exploded view;

FIG. 10 is a cross section view taken along the plane 10—10 of the connector assembly of FIG. 9;

FIG. 11 is an exploded perspective view of the connector assembly of FIG. 8;

FIG. 12 is an exploded plan view of the connector assembly of FIG. 8 showing the pylon of the further embodiment of this invention in an angular orientation with respect to the base member;

FIG. 13 is a cross section view taken along the plane 13—13 of the connector assembly of FIG. 12;

FIG. 14 is an enlarged cross section view of the connector assembly of this invention showing the pylon and base member disposed in an angular engagement;

FIG. 15 is a bottom perspective view of the pylon of the connector assembly of FIG. 8;

FIG. 16 is a plan view of the pylon of the connector assembly of FIG. 8 shown in isolation;

FIG. 17 is a cross section view taken along the plane 16—16 of the connector assembly pylon of FIG. 16 showing a fastening means provided adjacent to the first end of the pylon;

FIG. 18 is an enlarged plan view of the insert of the connector assembly of FIG. 8 shown in isolation;

FIG. 19 is a cross section view taken along the plane 19—19 of the connector assembly insert of FIG. 18 without the internal securing nut;

FIG. 20 is a cross section view of the connector assembly insert of FIG. 18 with the securing nut disposed internally of the insert;

BEST MODES FOR CARRYING OUT THE INVENTION

Figures 2, 3:
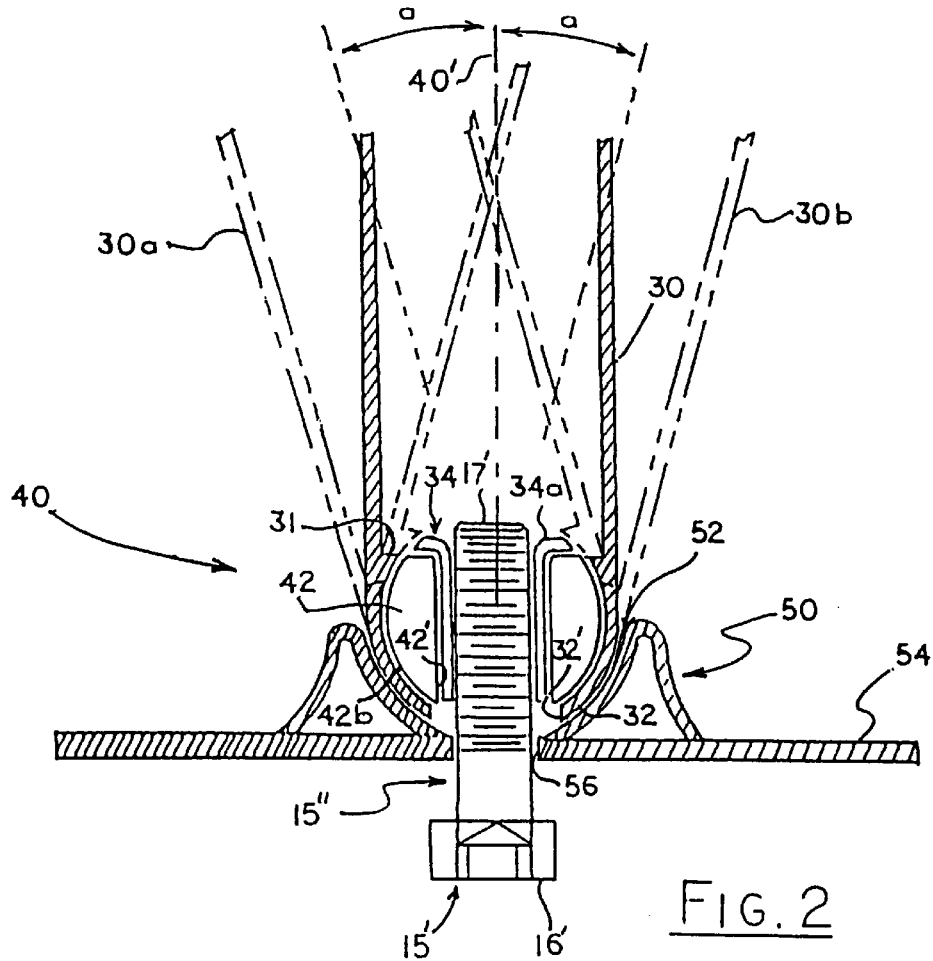
FIG. 2 is an enlarged detail cross-section of a connector system of this invention.
FIG. 3 is an enlarged detail cross-section of a further embodiment of a connector system of this invention.

Referring now to the drawings wherein like reference numerals designate identical or corresponding parts throughout the various views, FIG. 1 shows a prosthetic device 10 constructed in accordance with one preferred embodiment of the present invention. Prosthetic device 10 shown in FIG. 1 is designed for a below-the-knee (BK) amputation and thus includes no knee joint. However, the claimed invention is not limited to any particular limb for which a prosthesis is needed, nor is the invention necessarily limited to prosthetic systems.

Device 10 includes a prosthetic socket 12 for receiving a residual limb therein, a foam core 14 to provide a lightweight core for the inner and outer layers, a first connector system 20 interconnecting the socket 12 to the upper end of a prosthetic tube or pylon 30, and a second connector system 40 interconnecting the lower end of pylon 30 to a prosthetic foot 60.

As shown in FIGS. 1 and 3, connector system 20 of the invention more specifically comprises a spherical element such as a ball 22, a first prosthetic member defined by a tubular pylon adapter 23 having a first male end defined by a convexly hemispherically shaped end 24, and a second prosthetic member 25 having a concavely hemispherically (bowl-like) shaped female contact surface 26 for receiving therein the male end 24 of adapter 23. Connector 20 further includes an extending member 15 defined by a prosthetic bolt having a proximal end 16 and a distal end 17. The distal end 17 extends through an opening 26 provided in the second prosthetic member 25 and an opening 24' disposed in the male end 24 of adapter 23 to be received through a diametrical bore 22' provided in ball 22. Distal end 17 of bolt 15 is externally threaded and is received within an internally threaded insert 34 disposed within the bore 22' of ball 22.

Ball 22 has a planar surface 22a on one side and threaded insert 34 has a radial shoulder 34a, the underside of which abuts the planar surface 22a of ball 22. Ball 22 has a spherical surface 22b which bears against the concavely spherical interior surface of radiused end 24.

Adapter 23 also includes a shoulder 23a, which retains ball 22 within the first end 24 of adapter 23, and as shown in FIG. 1, provides an abutment means against which the upper end of pylon 30 rests when received within adapter 23. Second prosthetic member 25 includes a base 25a that, in the connector system 20 as shown in FIG. 1, can be trimmed as needed and affixed to a limb socket 12. If desired, the entire prosthetic seat member 25 may be integrally molded in the prosthetic socket.

Adapter 23 is secured to the upper end of pylon 30 via tightening or fastening means 23' which, when tightened, decreases the diameter of adapter 23 slightly so as to increasingly bear against the upper end of the pylon 30 in a clamping fashion. Fastening means 23' includes a sleeve 23b to prevent damage to the composite material from which adapter 23 is constructed. Sleeve 23b also includes a threaded portion for receiving the threaded end of the fastener as is known in the art.

Figure 4:
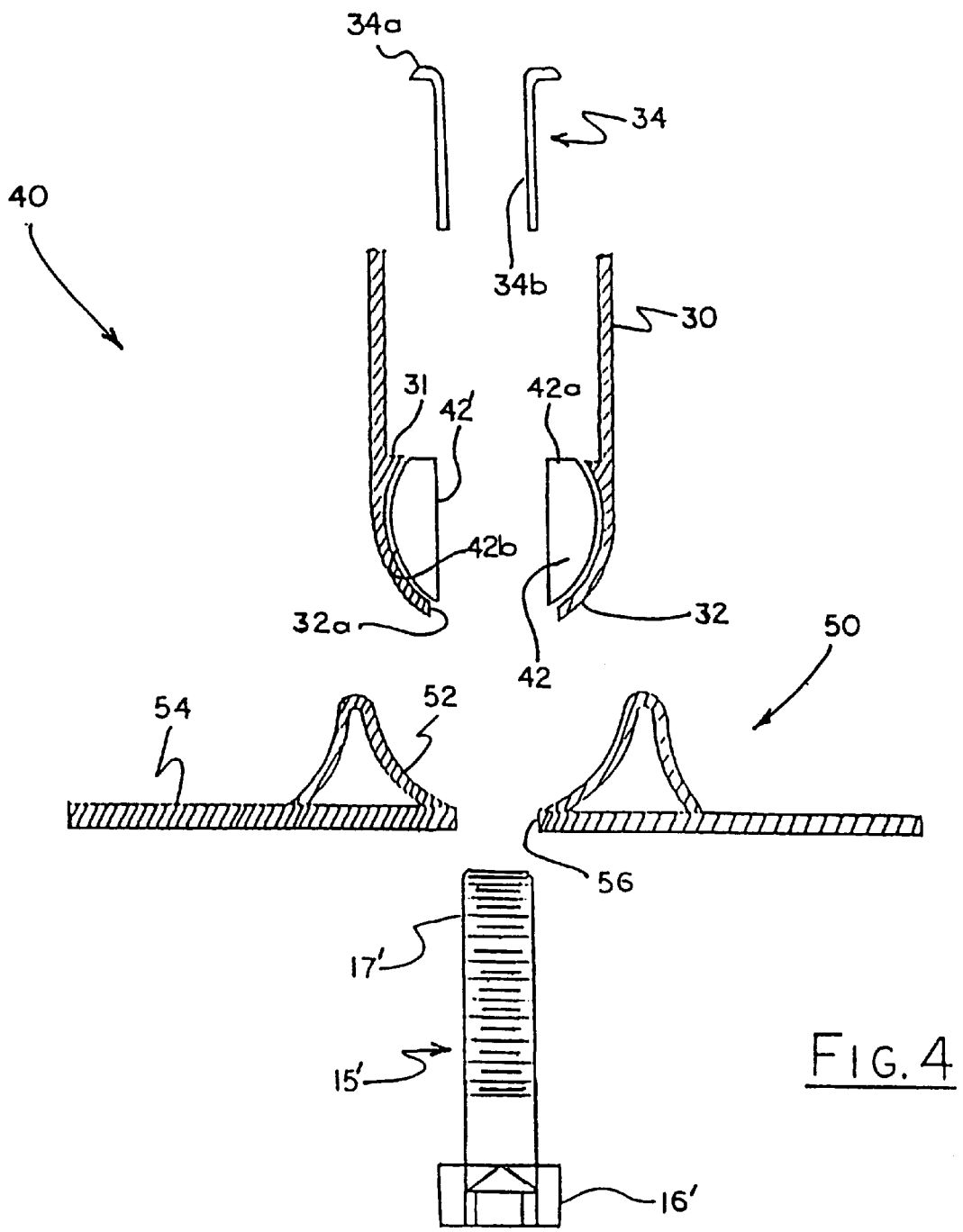
FIG. 4 is an exploded cross-section of the connector system of FIG. 2.

Connector system 40 interconnects the lower end of pylon tube 30 with the prosthetic foot 60 and is similar in structure to upper connector system 20, except system 40 includes a first prosthetic member defined by pylon 30 instead of the adapter 23 employed with upper connector system 20. Accordingly, as best shown in FIG. 4, connector system 40 includes a spherical element such as a ball 42, a first prosthetic member defined by pylon 30 having a first end defined by a convexly hemispherically shaped male end 32, and a second prosthetic member 50 having a concavely hemispherically shaped female contact surface 52 for receiving therein the male end 32 of pylon 30. Second prosthetic member 50 also includes a base 54 which can be affixed by conventional adhesives to a foot plate 62 of a prosthetic foot 60. Base 54 may be trimmed as needed to fit the dimensions of the foot plate 62 of foot 60. Alternatively, the entire prosthetic seat member 50 can be integrally molded atop a prosthetic foot.

Connector system 40, like connector system 20, includes an extending member defined by a prosthetic bolt 15' having proximal end 16' and a threaded distal end 17'. Bolt 15' is slightly longer than bolt 15 of connector 20 to accommodate the foot plate 62 of foot 60 as shown at 15". The distal end 17' extends through an opening 56 provided in the second prosthetic member 50, and through an opening 32a provided in the male end 32 of pylon 30 to be received through a diametrical bore 42' provided in ball 42. Distal end 17' of bolt 15' is externally threaded and is received within insert 34 disposed within the bore 42'. Insert 34 is provided with internal threads at 34b.

Ball 42 also has a substantially planar surface 42a on one side against which abuts the radial shoulder 34a of insert 34. Ball 42 includes a spherical surface 42b which bears against the concavely spherical interior surface of radiused end 32 of pylon 30. End 32 also includes an internal lip or shoulder 31 which retains ball 42 within the first end 32 of pylon 30.

The tightening of bolt 15' applies a clamping force on the radiused end 32 of pylon 30 against seat surface 52. This provides prevailing torque to prevent the pylon 30 from tilting when a bending force is applied. When bolt 15' is loosened, the pylon tube 30 may be tilted or rotated in any direction to provide quick and easy adjustment. As shown in FIG. 2, tube 30 is tiltable up to an included angle "a" of approximately 15 degrees as shown by phantom FIGS. 30a and 30b. Pylon 30 may be rotated through a full 360 degree pattern. The spherical exterior surface of the male end 32 slides between the mating hemispherical surfaces 42b and 52 of ball 42 and prosthetic seat 50, respectively, as best seen in FIG. 4. To this end, opening 32a in the male end 32 of pylon 30 should be sufficiently larger in diameter than bolt 15' to allow for the pylon 30 to be tilted; otherwise, if the circumferential edge of opening 32a abutted against or was distanced only slightly from the bolt shank, such an arrangement would in effect "lock" the end 32 of the pylon 30 and prevent any tilting movement of pylon 30.

During any movement of pylon 30, the orientations of ball 42 and seat 50 remain stationary relative to a longitudinal axis 40' of connector 40 due to the fixed orientation of bolt 15' with respect to the prosthetic seat 50 and ball 42. The pylon 30 may then be readily locked in a fixed position relative to the seat 50 and axis 40' by tightening bolt 15' to threadably engage insert 34.

Connector system 20 works in a substantially similar fashion wherein the tightening of bolt 15 engages the threaded insert 34 to pull the insert toward the proximal end 16 of the bolt, which clamps the male end 24 of adapter 23 between the ball 22 and the contact surface 26 of seat 25. Connector system 20 includes adapter 23 so that in custom fitting a patient, the prosthetist determines the appropriate length required for pylon 30 and cuts off any unnecessary length. This allow the pylons of this invention to be manufactured in standard lengths that may then be sized as needed when fitting the patient.

After the prosthetic has been fitted and all angular adjustments made to accommodate the particular physiological characteristics of the patient, an urethane or epoxy adhesive may be applied if desired at the interface of the male ends 24, 32 of adapter 23 and pylon 30, respectively, and the contact surfaces 26 and 52 of prosthetic seats 25 and 50, respectively, to further ensure the fixed rigidity of the connections for the prosthetic device 10.

The preferred material used for the ball 22, 42 is a thermoplastic material, such as DELRIN or nylon, provided with a threaded insert 34, or the ball can be constructed of a light-weight metal such as aluminum, which is then diametrically bored and threaded ⅜" ½-16—a standard thread for a prosthetic bolt. The thermoplastic ball is preferably ½" to 1 ½" in diameter depending on the patient. In the prosthetic system 10 of FIG. 1, the upper ball 22 preferably has a diameter of about 1 ⅛ inches, while the lower ball 42 has a diameter of about 1 inch. Children typically use small components and heavy or active adults typically use larger components. The thermoplastic ball is machined flat on one side to provide a substantially planar surface (22a, 42a) and drilled perpendicular to that plane to provide a diametrical bore (22' and 42'), which accommodates the T-nut-type threaded insert 34. The insert can be pressed in, bonded with adhesive, ultrasonically welded, or the like. When the fastening bolt is tightened, the plastic ball is plastically deformed to exert pressure on the inside radius of the male end of the pylon tube to provide the clamping force which locks tube 30 or adapter 23 in position.

The pylon tube 30, shown separately in FIGS. 7A and 7B, is formed from winding composite filaments on to a tooling rod (mandrel) preferably made of polished steel, a plastic material, or silica sand/PVA mixture, using a NC-controlled filament winding process. Alternatively, the pylon tube 30 can be constructed of pre-impregnated materials that can be hand-laid on the prosthetic mold. Pylon 30 has a thickness of about 0.060 inches. The tooling mandrel has flat ends (90° to long axis), threaded studs on each end that are compatible with the threaded insert 34, and a slot in the middle with a replaceable bushing that can be cut against with a composite machining tool. The mandrel may unscrew at its mid-part for easy part removal. A ball (22, 42) is screwed onto each end of the mandrel with the top shoulder 34a of the insert 34 abutting against the flat end of the mandrel. A bushing is then applied over the threaded end of the mandrel against the bottom of the ball, which is beveled on its outside diameter to retain the fiber filaments at the radius end. The bevel is designed to the required radius and thickness as the expected composite thickness. The inside diameter of the bushing is also beveled so that the bolt 15 that screws into the insert is allowed clearance at openings 24' and 32' as the tube tilts up to 15°. The bushing is retained by a nut or a threaded washer.

The mandrel is preferably the same diameter as the ball and has a groove between the bottom half of the ball and the end of the mandrel. This groove is filled with composite during the winding process creating a reverse radius defining retaining lip or shoulder 23a and 31 that permanently retains the ball within the first end of the tube 32 after winding is completed. The mandrel will then have a two to four degree draft angle from the mid-shaft toward each end to facilitate the removal of the mandrel from the tube. The threaded insert 34 in the ball also helps the mandrel to be pushed out as it is unscrewed. The mandrel and two balls will have a geometry identical to a mandrel for a filament wound pressure vessels (except for the groove). This configuration makes it possible to manufacture two ball-tube components concurrently if desired, thus making higher production levels possible.

While winding patterns already exist for this geometry, the winding patterns employed to construct the pylon tube 30 of this invention can be varied many ways. For example, a variety of hoop and helical winding patterns can be used to achieve strength to resist tensile, compressive, and bending moments on the pylon tube, as well as clamping pressures on the radiused end and top of the tube. Carbon-epoxy and fiberglass-epoxy are preferred materials in the construction of pylon tube 30 and adapter 23. If necessary, the tube can be wound with extra material so that the tube can be machined to the desired outside diameter.

A shorter version of the two-ball mandrel with a diameter tolerance such that the finished part will fit over the tube at the top is needed to fabricate a two ball-tube adapter. The tube adapter will have a screw, sleeve, and nut wound into it. After the wound parts are removed from the mandrel, the tube adapter is cut longitudinally so that the sleeve and screw head will be on the opposite side of the slot from the nut. This will allow the screw to reduce the circumference of the tube adapter, thus creating a clamping force on the tube. This will allow length adjustments to the system by cutting the tube as needed to custom fit the patient.

The prosthetic seat (25, 50) is made of a composite, a thermoplastic, a light-weight metal, or a combination of those materials. The weight bearing contact surfaces 26, 52 of the seats are toleranced to fit the male radiused ends of the pylon tube and the adapter. Clearance and reverse radius will be provided to allow the tube to tilt up to 15°. A hard point is necessary at openings 26, 56 to prevent the fastening bolt from collapsing or damaging the seat from where it applies pressure about the circumferential area adjacent the openings.

In operation, the existence of two connector mechanisms 20, 40, one at the foot and one at the limb socket of prosthetic device 10, allows for all of the necessary adjustments in prosthetic alignment procedures to be made. These adjustments include primarily movement of the upper limb socket 12 in relationship to the foot 60. Such movements are anterior or posterior tilt, medial or lateral tilt, anterior or posterior slide, medial or lateral slide, and internal or external rotation. Length adjustments are, as noted above, made by removing the adapter 23 and cutting the pylon tube 30 as needed. After alignment adjustments are made, the bolts beneath the foot and in the bottom of the socket are tightened to "lock-in" the alignment of the prosthetic device 10. One very helpful feature is that with a hex-head wrench, the patient is able to adjust the heel height of the foot 60 himself to fit different shoes. This has previously been accomplished by using lifts placed in the shoe. Moreover, later adjustments to the alignment of device 10 maybe readily made via the two bolts 15 and 15' without disrupting the cosmesis of the prosthesis 10. This gives an amputee adjustable heel height which allows for more shoe choices and for greater comfort in shoeless walking.

The interface between the radiused end of the first prosthetic member (tube 30 or adapter 23) and the second prosthetic member seat 25 and 50 is of concern because these surfaces have a great potential for wear and slippage. If desirable, an interface material, such as an elastomeric or neoprene washer 70 shown in FIGS. 6A and 6B can be employed therebetween. Such friction-enhancing means like elastomeric washer 70 can include an opening 72 through which the fastening bolt extends.

Alternatively, surface finishes such as polyurethane coats can be employed to protect the composite tube and create enough friction at the interface to prevent slippage during walking. Moreover, energy storing feet have a tendency to increase the bending moment at the ankle (the location of the lower connector mechanism 40), which increases the potential for slippage. This requires the prosthetist to study bolt torque settings in combination with the preferred interface materials during bending tests to achieve the right amount of prevailing torque to maintain the proper alignment of the prosthetic device during use.

Figure 5:
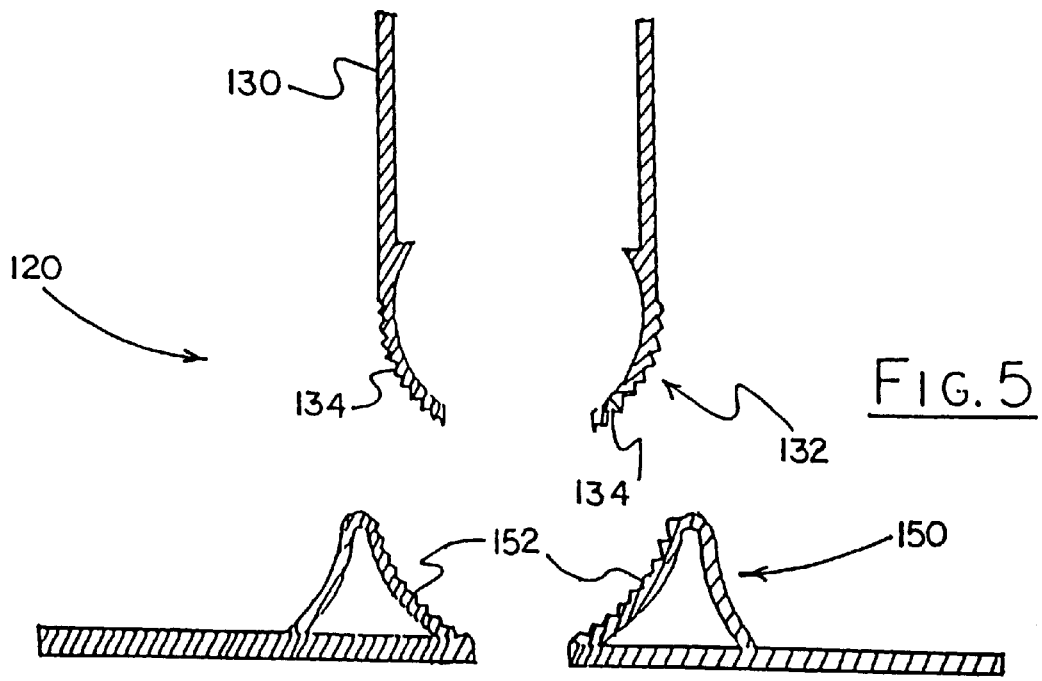
FIG. 5 is an enlarged detail cross-section of even a further embodiment of a connector system of this invention.

FIG. 5 shows a further alternative connector mechanism 120 provided by the invention wherein the exterior of first end 132 of pylon tube 130 is provided with a serrated, knurled or keyed surface 134 that interacts in an interlocking fashion with similar serrated or knurled surfaces 152 provided on the female weight bearing surfaces of prosthetic seat 150. In all other aspects, connector mechanism 120 is identical to connector mechanisms 20 and 40.

A further embodiment of the present invention provides a prosthetic joint connector assembly 100 shown in FIGS. 8–25 comprising a generally tubular pylon 130, an insert member 150 carried internally of pylon 130, a securing nut 170 carried internally of insert 150, a securing bolt 186, and an external base member 200.

Figure 22:
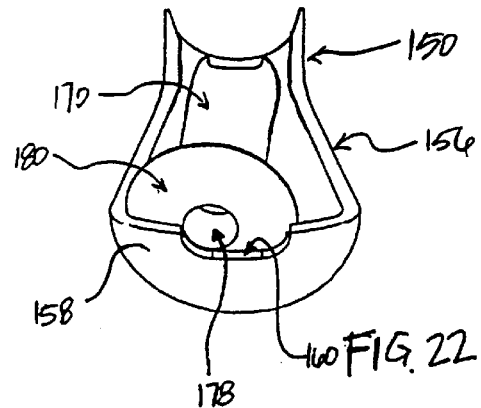
FIG. 22 shows the connector assembly insert in cross section and the internal securing nut in perspective from below.

The pylon 130 of this further embodiment, shown in isolation in FIGS. 16 and 17, has a generally cylindrical first end 132 and an outwardly flared portion 136 adjacent to its second or male end 134. The second end 134 of pylon 130 is partially closed by a convexly domed surface 138 having a non-circular opening 140 formed generally centrally therein. In a preferred embodiment, opening 140 is defined by a slot opening having rounded terminal portions, as best shown in FIGS. 15 and 22. Domed surface 138 concomitantly defines a concavely spherical interior surface 138'. Pylon 130 can further include fastening means 133 (FIG. 17) which, when tightened, slightly decreases the diameter of the first end 132 of pylon 130 so as to increasingly bear against the end of any prosthetic member inserted therein in a clamping fashion. Fastening means 133 includes a sleeve 133a to prevent damage to the composite material from which pylon 130 is constructed. Sleeve 133a also includes a threaded portion for receiving the threaded end of the fastener as is well known in the art.

The insert member 150 provided by the invention, shown in isolation in FIGS. 18–22, is carried internally by the pylon 130 and also has a generally cylindrical first end 152 and an outwardly flared portion 156 adjacent to its second end 154. The second end 154 of insert member 150 is partially closed by a convexly domed surface 158 having an opening 160 formed generally centrally therein. Opening 160 of insert member 150 has a slot shape with rounded terminal portions, which corresponds to opening 140 formed in the domed surface 138 of pylon 130. The domed surface 158 of insert member 150 also defines a concavely spherical interior surface 158'.

As one can see from the figures, the shape of the exterior of insert member 150 corresponds to and fits snugly within the interior configuration of the flared portion 136 and concave surface 138' of the second end 134 of pylon 130. As with the previous connector assembly embodiment described above in relation to FIGS. 1–7, the internal members of this further embodiment are permanently retained within the second and of pylon 130 as a result of the filament winding process by which the pylon is constructed. In the manufacture of this embodiment, the insert member 150 (once assembled carrying the securing nut 170 internally as discussed below) is placed upon the mandrel and the pylon 130 is then formed by winding composite filaments about the insert member in a predetermined pattern employing conventional NC-controlled winding processes known in the art and as discussed above with respect to the making of pylon 30 of FIGS. 1–7. As a result of this method of manufacture, the domed surface 158 of insert member 150 abuts and snugly engages the concave interior surface 138' of the second end 134 of pylon 130. The first end 152 of insert member 150 extends partially through the tubular portion of pylon 130 toward its first end 132 as shown in FIG. 10.

Figure 23:
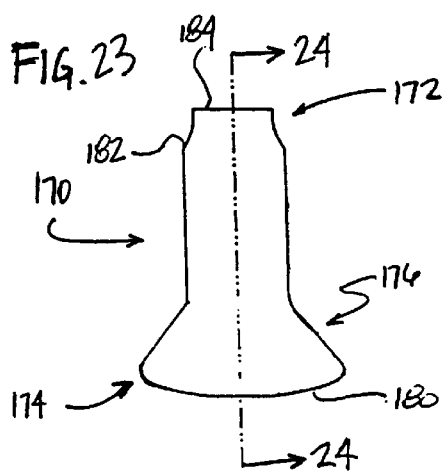
FIG. 23 is an enlarged plan view of the internal securing nut of the connector assembly of FIG. 8 shown in isolation.
Figure 24:
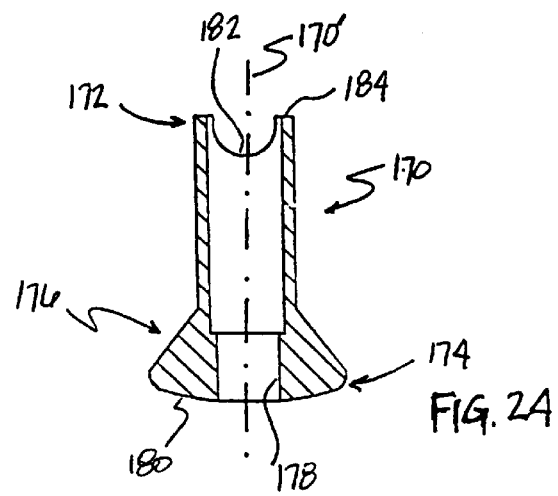
FIG. 24 is a cross section view taken along the plane 24—24 of the connector assembly securing nut of FIG. 23.
Figure 25:
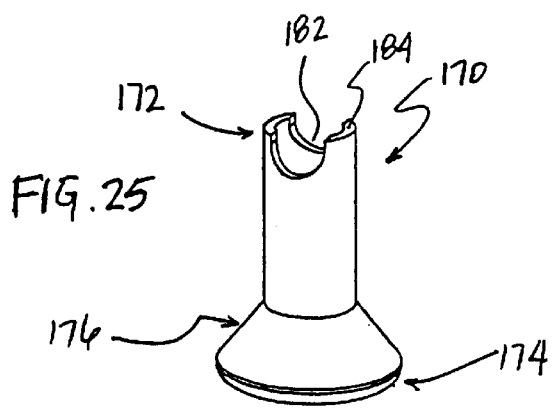
FIG. 25 is a perspective view of the connector assembly securing nut of FIG. 23.

The securing nut 170, shown in isolation in FIGS. 23–25, is carried internally of insert member 150 and has a generally cylindrical body at a first end 172, an outwardly flared portion 176 at a second end 174 thereof, and an internally threaded axial bore 178 extending from the second end 174 and at least partially along a longitudinal axis 170' (FIG. 24) of nut 170 toward its first end 172. The internally threaded axial bore 178 receives therein the externally threaded shank 188 of the distal end of securing bolt 186. The second end 174 of securing nut 170 also terminates in a convexly domed surface 180. When the securing nut 170 is disposed internally of the insert member 150, its convexly domed surface 180 abuttingly engages the concave interior surface 158' of the second end 154 of insert member 150.

Also in this further embodiment, as shown most clearly in FIGS. 19 and 20, an abutment 210 is disposed internally of the insert member 150 at a point generally coinciding with the juncture between the tubular first end 152 and outwardly flared portion 156 of insert member 150. The securing nut 170 is further provided with one or more bearing surfaces 182 at its first end 172 for engaging the abutment 210 and loosely and pivotally anchoring the first end 172 about abutment 210, which also prevents the securing nut from moving past the abutment 210 toward the first end 152 of insert member 150. In a preferred embodiment, such bearing surfaces 182 comprise diametrically opposing, inwardly disposed hemispherical relief portions formed in the first end 172 of nut 170 adjacent to yoke-like portions 184 (shown best in FIGS. 23–25). Yoke-like portions 184 extend partially around abutment 210 to prevent the first end 172 of nut 170 from disengaging therefrom, while still allowing nut 170 to freely pivot about the abutment 210 in a pendulum fashion. Securing nut 170 is made by conventional machining and thread-tapping techniques known in the art.

In the construction of insert member 150, which is constructed of a strong, light-weight material (preferably aluminum), a tubular portion defining the first end 152 of insert member 150 is permanently affixed to outwardly flared portion 156 to generally define a juncture 156a (FIGS. 18 and 19) between the two portions. The abutment 210 defined by a transverse bar extending diametrically across the interior space of the insert is then affixed in position. The securing nut 170 is then placed within the interior of insert 150 such that the first end 172 of nut 170 engages abutment 210 in a manner described above. A spherical or dish-shaped piece defining domed surface 158, which is formed by conventional stamping or coining techniques, is then affixed to close the open second end 174 of insert member 150. The preferred method of affixing or joining together the various elements of insert member 150 is by welding, but other conventional techniques may also prove suitable.

In such an arrangement, securing nut 170 is interposed between the abutment 210 and the concave interior surface 158' of insert member 150. In an even further embodiment, insert member 150 can be omitted and the domed surface 180 of nut 170 would bear directly against the interior surface 138' of the second end 132 of pylon 130. When not engaged by the securing bolt 186, the securing nut 170 is free to pivot at its first end 172 about the abutment 210 and, at its second end 174 and domed surface 180, to slidingly engage and move relative to the concave interior surface 158' of insert member 150 (or surface 138' of pylon 130). For example, as shown in FIG. 15, nut 170 moves within insert member 150 generally in a linear back and forth motion. Side-to-side (medial-lateral) motion of nut 170 is somewhat reduced by the bearing surfaces 182 and yokes 184 of the second end 172 of nut 170. The swinging motion of nut 70 and pylon 130 is predominantly in the anterior-posterior direction once the assembly is employed on a patient.

Referring now to FIGS. 8–14, the external base member 200 has a central opening 202 provided therein through which extends the shank 188 of securing bolt 186, and a concavely spherical bearing surface 204 for receiving the convexly domed surface 138 of pylon 130. Base member 200 can be constructed of a composite, plastic or metal material having sufficient strength to withstand a high-compression moment caused by the clamping forces created by securing bolt 186 and a bending moment caused by pylon 130 against bearing surface 204 Base member 200 is typically affixed to, or made an integral part of, an opposing prosthetic article, such as a prosthetic foot or limb socket such as those shown and discussed above in relation to FIG. 1.

Figures 6A, 6B:
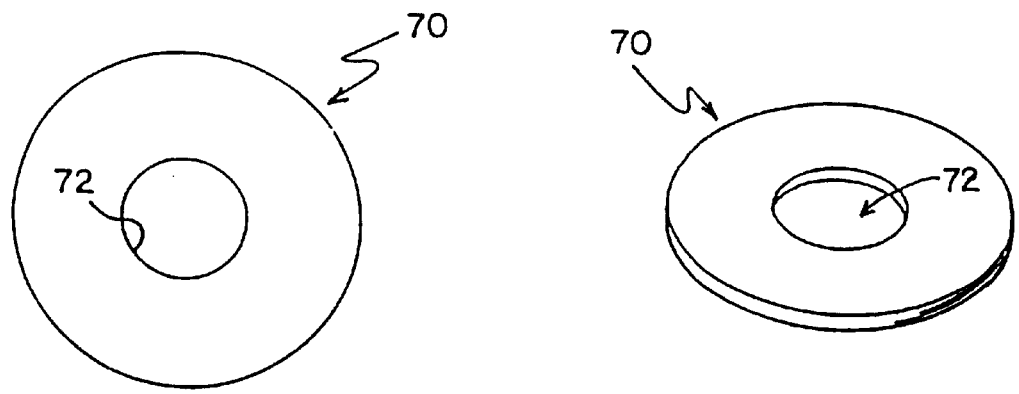
FIGS. 6A and 6B are top plan and perspective views, respectively, of a friction-enhancing element that can be utilized with the connector system of this invention.
Figure 21:
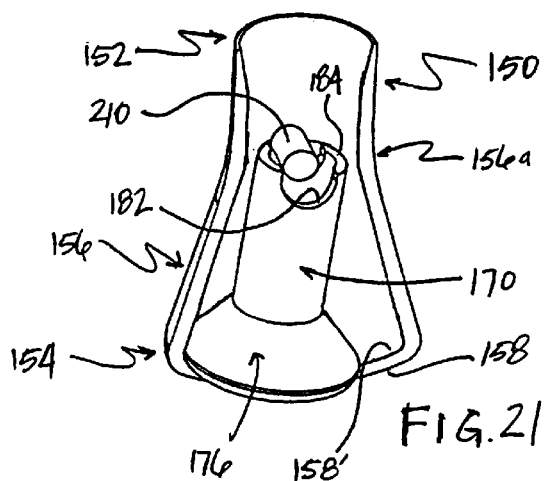
FIG. 21 shows the connector assembly insert and abutment in cross section and the internal securing nut in perspective from above.

In operation, once the prosthetist has determined the proper alignment of the artificial limb and the relative positioning of pylon 130 with respect to base member 200, the securing bolt 186 can be rotated to be threadably received in the internally threaded axial bore 178 of securing nut 170 to clamp with increasing force the domed surfaces 138 and 158 of pylon 130 and insert member 150, respectively, between the domed surface 180 of securing nut 170 and the bearing surface 204 of base member 200. To achieve oblique angular movements or a combination of posterior-anterior and medial-lateral movements, pylon 130 is rotated about its vertical axis until the long axis of slot opening 140 is oriented in the direction of the desired tilt, and the pylon is then tilted as desired. The tightening of securing bolt 186 releasably secures pylon 130 in position relative to the external base member 200 to maintain the proper alignment of the prosthetic device as determined by the prosthetist. If desirable, friction-enhancing means can be utilized at the interface between base member 200 and the domed surface 138 of pylon 130, such as an elastomeric or neoprene washer as shown in FIGS. 6A and 6B. Such friction-enhancing means like elastomeric washer 70 can include an opening 72 through which the securing bolt 186 extends. Alternatively, surface finishes such as polyurethane coats can be employed to protect the domed end of pylon 130 and create enough friction at that interface to prevent slippage or unintended movement during walking.

Bending tests to failure should always be performed to determine the limits for the pylons and connector assemblies of this invention. The compressive strength to failure of the pylons and of the radiused and domed ends of the first and second embodiments, respectively, can be tested on an Instron Model. Circumferential clamping tests should also be performed on the upper (first) ends of the pylon tubes. Impact testing of the pylon tubes is also necessary to ensure that energy released during an unintended fracture is not potentially dangerous to the patient. The prosthetic seat and base member should also be subjected to high clamping forces to test their off-axis crush strength.

The connector assemblies of this invention and the novel componentry are a radical change in design from present technology. The devices 10, 100 for below-knee amputees as shown in FIGS. 1 and 8 utilize advanced composites and materials with, preferably, an ultralight foot and prosthetic socket that results in a prosthetic device as light as 1.3 pounds or less. Such a drastic reduction in weight results in a reduction in energy expenditure and fatigue, better control, and increased mobility for the patient, which can mean the difference between walking or not walking for patients with low energy reserves, particularly geriatric patients. Moreover, by adding a small amount of additional composite material to the pylon as needed, the strength of the connector assemblies can be greatly improved, thereby making the device safe for very heavy and active patients. Smaller tooling of the same geometry can also be utilized to fit the assemblies of this invention to pediatric patients.

All angular and rotational adjustments of the embodiments of this invention can be readily made by simply accessing the securing prosthetic bolt. For example, in FIGS. 11 and 14, pylon 130 is tilted slightly to the left, which in use would be in the posterior direction or, more likely, the anterior direction, such that securing nut 170 is moved in a maximum displacement wherein its outer circumferential edge abuts the crotch formed by the junction of concave surface 138' and flared portion 156 of insert member 150. In the embodiment shown in FIGS. 8–25, the maximum angular displacement of pylon 130 with respect to a longitudinal axis extending through bolt 186 and base member 200 is about 6 degrees. When these inventions are employed in an artificial BK limb system, all such adjustments are available from outside the foam cover of the prosthesis.

Thus, this invention has a significant advantage over present systems in being able to provide lighter modular prosthetics with equal or greater strength. Another significant advantage is that all adjustments to the prosthetic alignment are available outside the cosmesis of the prosthesis. Development of other components such as ultralight knees, energy-storing pylons, and hip joints are possible because of this invention.

Although the devices provided by the present invention have been described with preferred embodiments, those skilled in the art will understand that modifications and variations may be made without departing from the scope of this invention as set forth in the following claims. Accordingly, such modifications and variations are considered to be within the purview and scope of the claims.

We claim:

1. A connector assembly for a prosthetic joint, comprising:
    a first means defined by a generally tubular member having a first end and an outwardly flared portion adjacent to a second end thereof, said second end being partially closed by a convexly domed surface having a generally axial opening formed therein, said convexly domed surface defining a concave interior surface;
    a second means smaller in all dimensions than and carried internally of said first means and defined by a generally cylindrical member having a first end and an outwardly flared portion adjacent to a second end thereof, said second end terminating in a convexly domed surface, said second means being disposed internally of said first means such that the convexly domed surface of the second end of said second means abuttingly engages the concave interior surface of the second end of said first means, said second means having an internally threaded axial bore extending at least partially therethrough initiating at the flared second end thereof; and
    a third means comprising an abutment disposed internally of said first means, said second means having a bearing surface at its first end for engaging the third means such that the second means is interposed between the third means and the concave interior surface of the second end of said first means, said second means being free, when unsecured, to pivot about the third means at its first end and to, at its second end, slidingly engage and move relative to the concave interior surface of the flared end of said first means.

2. The prosthetic joint connector assembly as in claim 1 wherein said third means comprises a transverse bar extending diametrically across the interior of said first means, and wherein the bearing surface disposed at the first end of said second means for engaging said transverse bar comprises inward relief portions defining yoke portions which extend partially about said abutment.

3. The prosthetic joint connector assembly as in claim 1 wherein said first means comprises a prosthetic pylon constructed from wound composite filaments.

4. The prosthetic joint connector assembly as in claim 1 wherein said first means is pivotable about its second end to a maximum angle with respect to a longitudinal axis of approximately six degrees.

5. The prosthetic joint connector assembly as in claim 1 wherein said first means further includes an adapter disposed at its first end, said adapter including releasable fastening means such that the activation of said fastening means causes said adapter to increasingly engage and releasably secure an end of a separate article within said adapter.

6. The prosthetic joint connector assembly as in claim 1 wherein said abutment is disposed internally of said first means at a point generally coinciding with the juncture between the tubular portion and outwardly flared portion of said first means.

7. The prosthetic joint connector assembly as in claim 1 wherein said opening formed in the domed surface of the second end of said first means is a non-circular opening.

8. The prosthetic joint connector assembly as in claim 7 wherein said non-circular opening comprises a slot opening having rounded terminal portions.

9. The prosthetic joint connector assembly as in claim 8 wherein the central point of said slot opening is disposed in general alignment with a longitudinal axis of said first means.

10. The prosthetic joint connector assembly as in claim 1 further comprising an external base means having a concavely spherical bearing surface, and
    wherein said second means defines a nut for, when receiving an externally threaded securing means therein, for clamping the domed second end of said first means between the second end of said second means and the bearing surface of said external base means, thereby releasably fixing said first means in position relative to said external base means.

11. The prosthetic joint connector assembly as in claim 10 wherein said external base means is affixed to or made an integral part of a prosthetic foot or a socket for receiving a residual limb.

12. The prosthetic joint connector assembly as in claim 10 wherein said external base means includes a central opening therein, and
    wherein a distal end of the securing means extends through the central opening of said external base means and is anchored thereat to prevent the securing means from disengaging from said external base means.

13. The prosthetic joint connector assembly as in claim 10 further comprising friction-enhancing means disposed at the interface between the convexly domed surface of the second end of said first means and the bearing surface of said external base means to inhibit any unintended relative movement between said first means and base means.

14. The prosthetic joint connector assembly as in claim 1 further comprising a fourth means carried internally of said first means, said fourth means comprising:
    a generally tubular member having a first end and an outwardly flared portion adjacent to a second end thereof, said second end being partially closed by a convexly domed surface having an opening formed therein, said convexly domed surface defining a concave interior surface, said fourth means being fixedly disposed internally of said first means.

15. The prosthetic joint connector assembly as in claim 14 wherein the convexly domed surface of the second end of said fourth means abuttingly engages the concave interior surface of the second end of said first means, the outwardly flared portion of said fourth means coincides with and is carried snugly within the outwardly flared portion of the first means; and wherein said third means extends diametrically across the interior of said fourth means disposed at a juncture of the outwardly flared portion of the second end and the tubular portion of the first end of said fourth means.

16. The prosthetic joint connector assembly as in claim 14 wherein said second means is defined by a securing nut for, when receiving an externally threaded securing means in its second end and upon the tightening of said securing means, for clampingly engaging the domed second ends of said first and fourth means between the second end of said second means and the bearing surface of said external base means for releasably fixing said first means in position relative to said external base means.

17. The prosthetic joint connector assembly as in claim 14 wherein said second, third and fourth means are permanently retained within the interior of said first means.

18. The prosthetic joint connector assembly as in claim 14 wherein said fourth means is constructed from a strong light-weight material.

19. The prosthetic joint connector assembly as in claim 14 wherein said fourth means is constructed of aluminum.

20. A prosthetic joint connector assembly, comprising:

a prosthetic pylon having a generally tubular first end and an outwardly flared portion adjacent to a second end thereof, said second end being partially closed by a convexly domed surface having an opening formed therein, said convexly domed surface defining a concave interior surface;

a securing bolt having a head and an externally threaded shank portion;

an insert carried internally of said pylon having a generally tubular first end and an outwardly flared portion adjacent to a second end thereof, said second end being partially closed by a convexly domed surface having an opening formed therein and defining a concave interior surface, said insert being fixedly disposed internally of said pylon wherein the convexly domed surface of the second end of said insert abuttingly and snugly engages the concave interior surface of the second end of said pylon and the outwardly flared portion adjacent to the second end of said insert generally coinciding with and being carried snugly within the outwardly flared portion of said pylon;

a securing nut carried internally of said insert having a generally cylindrical body at a first end thereof, an outwardly flared portion at a second end thereof, and an internally threaded axial bore initiating at the second end thereof and extending at least partially along a longitudinal axis of said securing nut toward the first end thereof for receiving therein the externally threaded shank of said securing bolt, said second end terminating in a convexly domed surface, said securing nut being disposed internally of said insert such that the convexly domed surface of the second end thereof abuttingly engages the concave interior surface of the second end of said insert;

an abutment disposed internally of said insert, said securing nut having a bearing surface at its first end for engaging said abutment such that the securing nut is interposed between the abutment and the concave interior surface of the second end of said insert, said securing nut being free, when unsecured, to pivot at its first end about said abutment and to, at its second end, slidingly engage and move relative to the concave interior surface of the flared end of said insert; and an external base having a central opening therein and a concavely spherical bearing surface for receiving therein the convexly domed surface of the second end of said pylon, said securing nut, upon rotatingly receiving the externally threaded securing bolt in the internally threaded axial bore thereof, clamping the domed second ends of said pylon and insert between the second end of said securing nut and the bearing surface of said external base, thereby releasably securing said pylon in position relative to said base.

* * * * *